United States Patent [19]

Leong et al.

[11] Patent Number: 5,759,582
[45] Date of Patent: Jun. 2, 1998

[54] CONTROLLED RELEASE OF PHARMACEUTICALLY ACTIVE SUBSTANCES FROM COACERVATE MICROCAPSULES

[75] Inventors: Kam W. Leong, Ellicott City, Md.; Rosa V. Azhari, Yuvalim, Israel

[73] Assignee: The Johns Hopkins University School of Medicine, Baltimore, Md.

[21] Appl. No.: 695,514

[22] Filed: Aug. 12, 1996

Related U.S. Application Data

[63] Continuation of Ser. No. 431,501, Apr. 28, 1995, abandoned, which is a continuation of Ser. No. 98,574, Jul. 28, 1993, abandoned.

[51] Int. Cl.$^6$ ............................................. A61K 9/50
[52] U.S. Cl. .................... 424/492; 424/490; 424/493; 428/402.2; 264/4.1; 264/4.3; 264/4.6
[58] Field of Search ........................ 424/490, 493, 424/492; 428/402.2; 264/4.1, 4.3, 4.6

[56] References Cited

U.S. PATENT DOCUMENTS

| | | | |
|---|---|---|---|
| 3,757,004 | 9/1973 | Brown et al. | 260/117 |
| 4,178,361 | 12/1979 | Cohen et al. | 424/22 |
| 4,794,000 | 12/1988 | Ecanow | 424/457 |
| 4,795,642 | 1/1989 | Cohen et al. | 424/455 |
| 4,923,645 | 5/1990 | Tsang et al. | 264/4.3 |
| 4,965,007 | 10/1990 | Yudelson | 252/62.53 |
| 5,051,185 | 9/1991 | Watanabe et al. | 210/635 |
| 5,051,304 | 9/1991 | David et al. | 428/402.2 |
| 5,089,272 | 2/1992 | Shioya et al. | 424/493 |
| 5,143,724 | 9/1992 | Leshchiner et al. | 424/78.08 |
| 5,260,002 | 11/1993 | Wang | 264/4.1 |

OTHER PUBLICATIONS

Azhari, et al., Protein Release from Enzymatically–Degradable Chondroitin–Sulfate/Gelatin Microspheres, Proceed. Intern. Symp. Control. Rel. Bioact. Master., 18:617–618, 1991, Controlled Release Society, Inc.

*Primary Examiner*—Jyothsan Venkat
*Attorney, Agent, or Firm*—Fish & Richardson P.C.

[57] ABSTRACT

A controlled-release pharmaceutical composition comprising a pharmaceutically active water soluble protein, peptide, glycoprotein, or mixture thereof, encapsulated in the form of microspheres by a coating of a crosslinked coacervate of gelatin and chondroitin sulfate, as well as processes for the preparation thereof.

6 Claims, 3 Drawing Sheets

CONTROLLED RELEASE OF PHARMACEUTICALLY ACTIVE SUBSTANCES FROM COACERVATE MICROCAPSULES

This is a continuation of application Ser. No. 08/431,501, filed Apr. 28, 1995, now abandoned, which is a continuation of application Ser. No. 08/098,574 filed on 7/28/93, now abandoned.

BACKGROUND OF THE INVENTION

1. Field of the Invention This invention relates to coacervate-based microcapsules which include pharmaceutically active substances as well as to a method of providing controlled release of such substances in vivo. The microcapsules of the invention are useful to prepare and deliver drugs, biologicals, enzymes, and pharmaceutically active substances.

2. Description of Related Art

A controlled delivery system which will dependably release a biologically active substance (e.g., a pharmaceutical agent) in vivo into a biological fluid (e.g., fluids of gastrointestinal tract) or into body tissues has remained an elusive goal. Biologically active endogenous substances such as cytokines, hormones, enzymes, and antibodies are usually less stable than conventional synthetic drugs in the physiological environment. The controlled delivery system thus provides a suitable means to administer these endogenous substances to a host.

A common approach to providing controlled release of the active substance is the encapsulation of the active substance within a polymer matrix (e.g., that made of hydrophilic polymers). While some combinations of a drug and particular polymers provide a suitable drug release profile, they require relatively large quantities of synthetic materials to be delivered to the body. This is not desirable since such materials or their metabolites in vivo may not be biocompatible or even may have toxicity such as cytotoxicity or mutagenicity. Furthermore, encapsulation involves the use of organic solvents and/or heat, both of which can be harmful to peptide or proteinous drugs, not to mention the above-described endogenous substances.

Complex coacervation is a process of separation of colloidal solutions into two or more immiscible liquid phases. When oppositely charged polyelectrolytes are brought to contact in aqueous medium, a spontaneous phase separation occurs with the result of formation of coacervates. The coacervate is a phase where colloids (e.g., polymers) are concentrated.

Coacervation has been employed to encapsulate water insoluble biologically active substances. For example, U.S. Pat. No. 4,794,000 discloses a method for preparing a pharmaceutical composition for oral administration which is based on two phase coacervate system where erythromycin is included as the active ingredient. U.S. Pat. No. 5,051,304 discloses microcapsules formed by coacervation between gelatin and a chemically depolymerized polysaccharide wherein a variety of water immiscible substances can be included.

While these and other references generally teaches the applicability of the coacervation technique to a delivery system in the form of a coacervate, the coacervate formation to encapsulate a particular substance of interest can only be achieved by carefully controlling the phase separation conditions such as the choice and concentrations of suitable polyelectrolytes, pH and temperature.

Rheumatoid arthritis, which affects 3–4% of the population, is characterized by inflammation and pain of joints. Although the etiology of rheumatoid arthritis is not well elucidated, both steroid and non-steroidal therapy have been used to alleviate the symptoms of this illness. However, gastrointestinal irritation, including ulcers, is a side effect commonly associated, to one degree or another, with anti-inflammatory agents. In order to avoid such side effects and to enhance drug concentrations in synovial sites, intra-articular injection is considered a viable method of administration of an anti-inflammatory agent. There appears to be no literature available which suggests coacervate-based microcapsules as a intraarticular form of administration of the anti-inflammatory agent.

The present invention permits desirable chemotherapy, including anti-inflammatory therapy, by providing controlled release of a pharmaceutically active substance into the body while preventing or ameliorating undesirable side effects associated with administration of the substance by a known delivery system.

SUMMARY OF THE INVENTION

In one aspect thereof, the present invention provides a pharmaceutical composition for the controlled release of a pharmaceutically active substance comprising a therapeutically effective amount of the pharmaceutically active substance in the form of microspheres, encapsulated by a coating of a crosslinked coacervate of gelatin and chondroitin sulfate.

In another aspect, the present invention also provides a process for preparing the above-described pharmaceutical composition which comprises the steps of:

(a) providing a gelatin aqueous solution;

(b) providing a chondroitin sulfate aqueous solution;

(c) adding a therapeutically effective amount of a pharmaceutically active substance either to the solution in step (a) or to the solution in step (b);

(d) mixing the gelatin and chondroitin sulfate solutions to form a coacervate suspension;

(e) adding a crosslinking agent to the coacervate suspension to crosslink the coacervates, the coacervates encapsulating the pharmaceutically active substance; and (f) incubating the coacervate suspension to form microspheres and recovering the microspheres.

In further aspect, the present invention provides a method of releasing a pharmaceutically active substance in vivo in a controlled manner which comprises administering the above-identified pharmaceutical composition to a host and degrading the coacervates by the action of a gelatin-digesting enzyme.

In still further aspect, the present invention provides an encapsulated pharmaceutically active substance. The above features and advantages of the present invention will be more fully understood by reference to the following detailed description and the drawings.

DETAILED DESCRIPTION OF THE INVENTION

Figure 1:
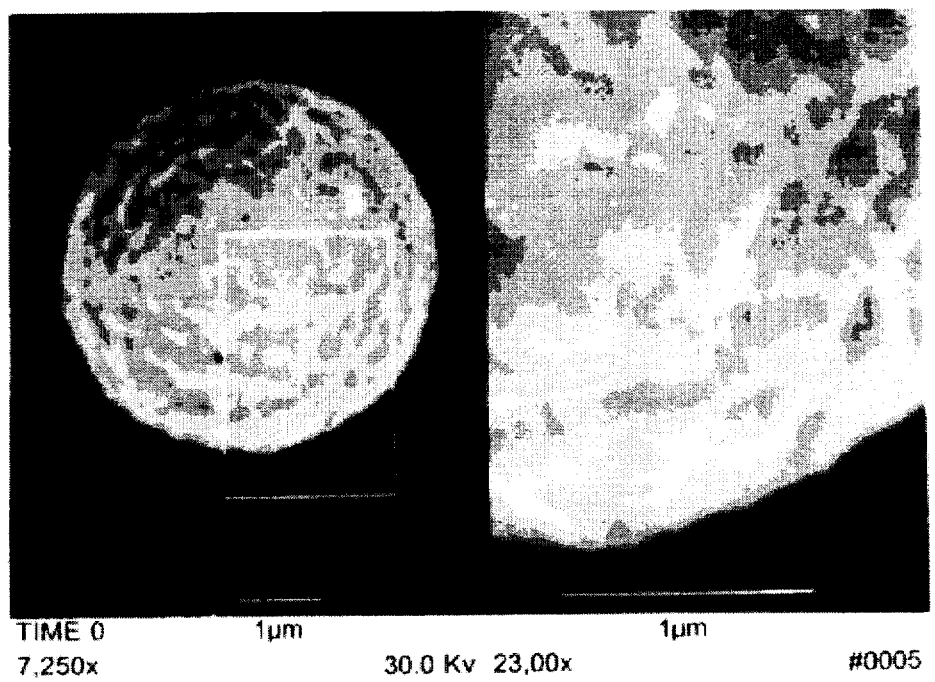
FIG. 1 is a photomicrograph of the microspheres prepared in the practice of the present invention.

In this disclosure, the term "microcapsules" refers to microspheres wherein a pharmaceutically active substance is encapsulated by a coating of coacervates. Specifically useful in the present invention is a solid microsphere which is a matrix type rather than a core-shell type. If the pharmaceutically active substance is a charged molecule such as protein, the molecule is likely to participate in the complex coacervation process to form the microsphere wherein the substance is entangled with the microsphere matrix.

As applied in the present invention, the term "pharmaceutically active substance" is intended to encompass any substance that will produce a therapeutically beneficial pharmacological response when administered to a host, both human and animal. Suitable substances include, but are not restricted to analgesics, antibacterials, antifungals, immunosuppressants, anti-inflammatories, and anti-cancer agents. Some non-limiting examples of antibacterials include penicillins, cephalosporins, tetracyclines, quinolones, and aminoglycosides. Representatives of anti-inflammatories include hydrocortisone, colchicine, ibuprofen, indomethacin, and piroxicam. More than one pharmaceutically active substance may be included, if desired, in the pharmaceutical compositions of the present invention. The active substances may be water-soluble or water-insoluble and may include those having a high molecular weight proteins, peptides, carbohydrates, glycoproteins, lipids, and glycolipids. The process of the present invention is particularly suitable for encapsulation of these high molecular weight, susceptible biomacromolecules.

The pharmaceutically active substance can be employed in the present invention in various forms, such as molecular complexes or pharmaceutically acceptable salts. Representative examples of such salts are succinate, hydrochloride, hydrobromide, sulfate, phosphate, nitrate, borate, acetate, maleate, tartrate, salicylate, metal salts (e.g., alkali or alkaline earth), ammonium or amine salts (e.g., quaternary ammonium) and the like. Furthermore, derivatives of the active substances such as esters, amides, and ethers which have desirable retention and release characteristics but which are readily hydrolyzed in vivo by physiological pH or enzymes can also be employed.

As used herein, the term "therapeutically effective amount" means that the amount of the pharmaceutically active substance is of sufficient quantity to induce desired pharmacological effect. The amount can vary greatly according to the effectiveness of a particular active substance, the age, weight, and response of the individual host as well as the nature and severity of the host's symptoms. Accordingly, there is no upper or lower critical limitation upon the amount of the active substance. The required quantity to be employed in the present invention can readily be determined by those skilled in the art.

As used herein with respect to the pharmaceutically active substance, the term "controlled release" is intended to mean that the present composition require at least an hour to release a major portion of the active substance into the surrounding medium, e.g. about 1-24 hours or even much longer.

In accordance with the present invention, the pharmaceutically active substance is encapsulated in a coacervate which is reinforced by crosslinking. Components that may be used to form the coacervate comprise anionic and cationic molecules. By "cationic" or "anionic" molecule is meant a molecule which, under the conditions of coacervation, carries a net positive or negative charge. Many such molecules are amphoteric and contain both acidic and basic groups. Under prevailing pH conditions, these molecules can be either cationic or anionic. Cationic molecules include albumin, collagen, elastin, gelatin, and globulins. Anionic molecules include chondroitin sulfate, dermatan sulfate, heparin, heparan sulfate, hyaluronic acid, keratan sulfate, polygalacturonic acid, and polyglucuronic acid. The choice of the cationic and anionic molecules depends on the final or intended use of the present compositions and they are expected to possess a high degree of biocompatibility. Preferably, gelatin is used as the cationic molecule in the present invention. Collagen is also preferred as the cationic molecule. Chondroitin sulfate is preferably used as the anionic molecule. Chondroitin sulfate is a mucopolysaccharide found in skeletal and soft connective tissues. The crosslinking is preferably effected by use of a gelatin-harding agent such as glutaraldehyde. Epichlorohydrin and acrolein can also be used as the crosslinking agent. Typically, in preparing the coacervates of the present invention, both types of components are brought into contact in an aqueous medium under predetermined mixing conditions. The mixing can conveniently be carried out using equivolumes of an aqueous gelatin solution and an aqueous chondroitin sulfate solution. Preferably, gelatin is present in the aqueous solution in a concentration of from about 1% to about 10% (w/vol). Chondroitin sulfate is present in the aqueous solution in a concentration of from about 0.05% to about 2% (w/vol). Outside these concentration ranges, the formation of coacervates appears to be adversely effected.

The temperature to be employed in forming coacervates may vary somewhat with the particular method employed. Thus, a temperature from ambient temperature to about 50° C. can normally be used. However, the size of coacervates is susceptible to the temperatures of the two components when they are mixed. The higher the temperature of the gelatin solution, the smaller become the coacervates formed. The pH to be employed in forming coacervates can also vary over a fairly wide range. The yield and size of coacervates are influenced by the pH. Preferably, the pH of from about 3.5 to about 6.5 (the latter of which corresponds to the isoelectric point of gelatin) is used. The pH of the gelation solution predominates over that of the chondroitin solution in determining the pH of the mixture of the two. Optimum results in terms of both the size and yield of the coacervates are obtained at a pH of about 5.0.

The desired amount of the pharmaceutically active substance is added either to the gelatin solution or to the chondroitin sulfate solution prior to the formation of coacervates. If the active substance is water-soluble, a solution results. On the other hand, if the active substance is water-insoluble, an emulsion or suspension results.

Upon mixing of the gelatin solution and the chondroitin sulfate solution with stirring, coacervation takes place in the reaction medium to form coacervates of microsphere. Since a coating of coacervate (walls) is generally too fragile for coacervates to be isolated, the crosslinking of the coacervates is necessary. The crosslinking is preferably carried out by adding to a suspension containing stabilized coacervate-coated microspheres, glutaraldehyde or another gelatin hardener. After completion of the crosslinking reaction, the resulting microspheres are recovered from the reaction medium by a conventional means, e.g., decantation, filtration, or centrifugation. The microspheres may be washed and dried in a standard technique, e.g., lyophilization.

The coacervate-coated microspheres of the present invention preferably have a sphere size (mean diameter) of about 0.5 μm to about 100 μm, and contain about 10% to 40% (w/w) of a pharmaceutically active substance. In other words, the weight ratio of the pharmaceutically active substance to the coacervate (walls) in the microspheres on a dry basis is about from 1:9 to about 2:3. The pharmaceutical compositions based on the coacervate-coated microspheres can be utilized for oral ingestion, implantation, or external application to the skin or a mucous membrane. Where implantation is desired, they can be implanted subcutaneously, constitute a part of a prosthesis, or be inserted in a cavity of the human body. Subcutaneous implantation using a syringe consists of injecting the implant directly into subcutaneous tissue, and is a particularly effective method of controlled drug delivery. This method is viewed as an alternative to surgery where some risk may be encountered. Thus, the microcapsules obtained in the present invention can be suspended in a physiological buffer and introduced via a syringe to the desired site.

For example, the present compositions incorporating hydrocortisone or any other known anti-inflammatory agent can be injected into the region of an inflammatory joint or muscle. As indicated above, a wide variety of pharmaceutical agents can be included in the present compositions and administered to the body in essentially the same manner. Other than anti-inflammatories, the delivery of narcotic antagonists, contraceptive or anabolic steroids, and anticancer agents can be contemplated. Narcotic antagonists, such as naltrexone, cyclazocine, and naloxone, are therapeutically useful in the postdetoxification stage of rehabilitation of drug-dependent patients. Steroids which can be used are, for example, progesterone and estradiol. Anticancer agents which can be used include cyclophosphamide, 5-fluorouracil (5-FU), doxorubicin, and cisplatin. Additionally, intravaginal or intraureteral implants based on the present compositions may be useful for the delivery of contraceptives and other drugs.

Upon application to the desired part of the body by the desired mode, the pharmaceutical compositions of the present invention provide controlled release of the pharmaceutically active substance by allowing it to diffuse through the coacervate walls of microspheres or by allowing the coacervate to degrade in vivo upon contact with body fluids. When the coacervate is degradable in the site (e.g., tissue or joint) where the composition is delivered, the degree of its degradation (i.e., the release rate of the active substance) can be regulated by the crosslinking degree of the coacervate.

The microcapsules of the present invention is premised primarily upon components which are found endogenous to the human body, whether natural or synthetic. The present invention thus makes it possible to employ significantly lesser quantities of non-biological materials than generally used in preparing controlled release pharmaceutical compositions. This high level of biocompatibility reflects in the absence of cytotoxicity and immunogenicity and the lack of causation of inflammation and foreign body reaction.

The following non-limiting examples are provided to further illustrate the present invention.

EXAMPLE 1

In this example, the following reagents and solvent were used: Gelatin (type A, 60 bloom; Sigma, St. Louis, Mo.), chondroitin-4-sulfate (Sigma), glutaraldehyde (Sigma), collagenase (type VII; Sigma), fluorescein isothiocyanate (FITC; Sigma), sCR1 (*T Cell Sciences*, Cambridge, Mass.), 2,2'-azino-di-[3-ethyl benzthioazoline-6-sulfonic acid] (ABTS; Bio-Rad, Hercules, Calif.), and sheep red blood cells (Thomas D. Morris, Inc., Philadelphia, Pa.).

sCR1 (22 mg) was dissolved in 5 ml of 0.2% (w/v) chondroitin sulfate in distilled water at ambient temperature. An equal volume of 5% (w/v) gelatin in distilled water at 37° C. was added to the chondroitin sulfate solution. Upon mixing by a vortex mixer, a suspension was obtained and this was stirred for 10 minutes. Glutaraldehyde (5 μl/ml) in distilled water was added to the suspension. The mixture was shaken in a rotary shaker for 30 minutes at room temperature. Ethanolamine-HCl (pH 9.0, 0.6 ml/ml solution) was added to the mixture in order to quench the excess glutaraldehyde. The resulting mixture was allowed to stand overnight at 0° C., precipitating microparticles. The microparticles were collected, washed with phosphate buffered saline solution (PBS; 0.01M, pH 7.4), and dried.

The morphology of the microparticles' surface was determined by scanning electron microscope (SEM). Samples were dried using $CO_2$ critical point drying and then sputter coated with gold. SEM images were taken at 20 to 30KV on an Amray 1810 microscope. Under SEM, the microparticles were determined to be spherical and to have a particle size of between 5 μm and 30 μm.

The amount of sCR1 encapsulated in the microspheres was determined by analysis in solution before and after encapsulation. The analysis was conducted according to an ELISA procedure using monoclonal Mouse IgGI anti-sCR1 and a peroxidase conjugate of Sheep anti-Mouse IgG. ABTS was used as the peroxidase substrate. Thus, a sCR loding level of about 35% (w/w) was determined.

A confocal microscope (Bio-Rad MRC-600 microscope) study was undertaken to determine the distribution of sCR1 within the microsphere.

For this purpose, fluorescein labelled sCR1 was synthesized by addition of 5 mg of FITC (dissolved in 0.5 ml of acetone) to 3.6 mg of sCR1 in 3 nl of 0.1M sodium bicarbonate. After reaction at room temperature for 15 minutes and at 0° C. overnight, the mixture was dialyzed against water and lyophilized.

sCR-FITC was encapsulated substantially in the same manner as that described above. A photomicrograph of the microsphere showed that sCR1 -FITC is uniformly distributed throughout the microsphere with a slightly lower concentration toward the outer surface.

A similar analysis using FITC-labelled gelatin showed that the microspheres are of a matrix type and not a core and shell type.

sCR1 is a recombinant, soluble, human complement receptor 1 (CR1) which has been shown to retain the activity of CR1 both in vitro and in vivo (J. M. Ahearn, et al., *Advances in Immunology*, 1989, 46, 183–219; H. F. Weisman, et al., *Science*, 1990, 249, 146–151). CR1 is an endogenous regulatory protein that blocks proteolytic enzymes which activate complement proteins $C_3$ and $C_5$. Administration of sCR1 will interfere with the complement activation, thus averting destructive biological processes which lead to inflammation and damage to cartilages. sCR1 is a high molecular weight (200 KD) protein with a half life shorter than 15 minutes at physiological conditions. Thus, the use of sCR1 in its native form as an anti-rheumatic agent will require frequent intra-articular injections. Encapsulation of the protein within microspheres can provide adequate protection in the joint cavity, introduce controlled release features and reduce the frequency of intra-articular injections needed.

EXAMPLE 2

IN VITRO DRUG RELEASE FROM MICROSPHERES

Release experiments were conducted in 20 ml of PBS containing 0.36 mM calcium chloride and 10 units of collagenase. The microspheres prepared according to the procedure of EXAMPLE 1 (27 mg dry weight) were suspended in the PBS solution and incubated at 37° C. Control samples were also prepared in the absence of collagenase.

Figure 2:
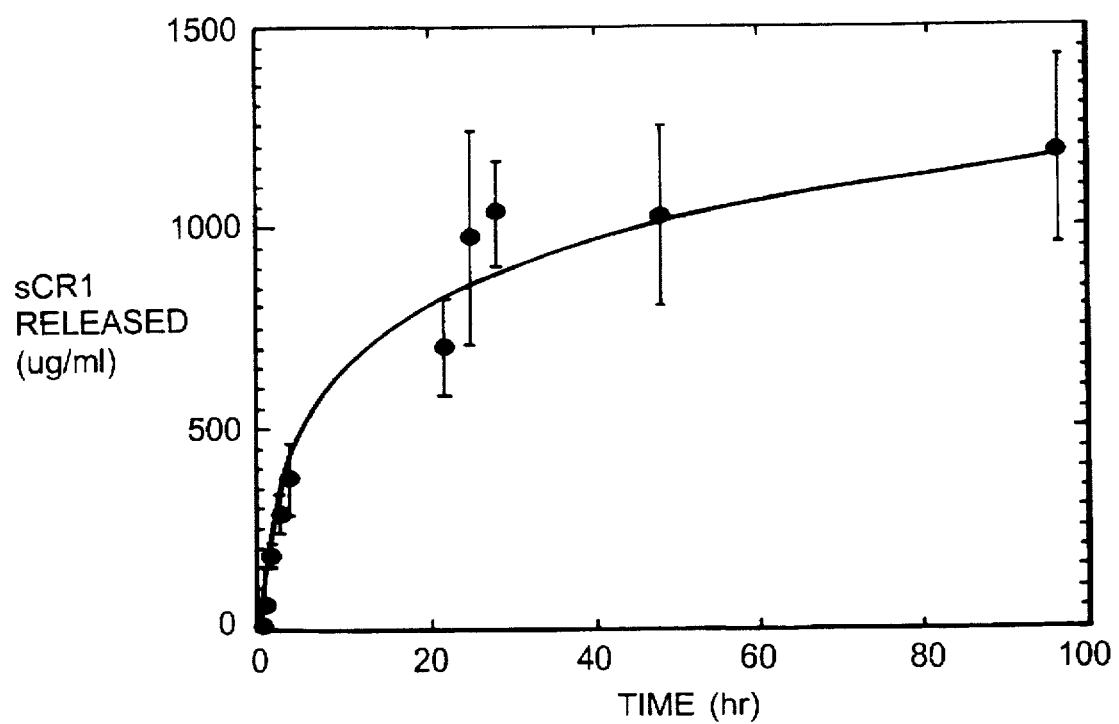
FIG. 2 shows the in vitro release kinetics of sCR1 when incorporated in the pharmaceutical composition according to the present invention.
Figure 3:
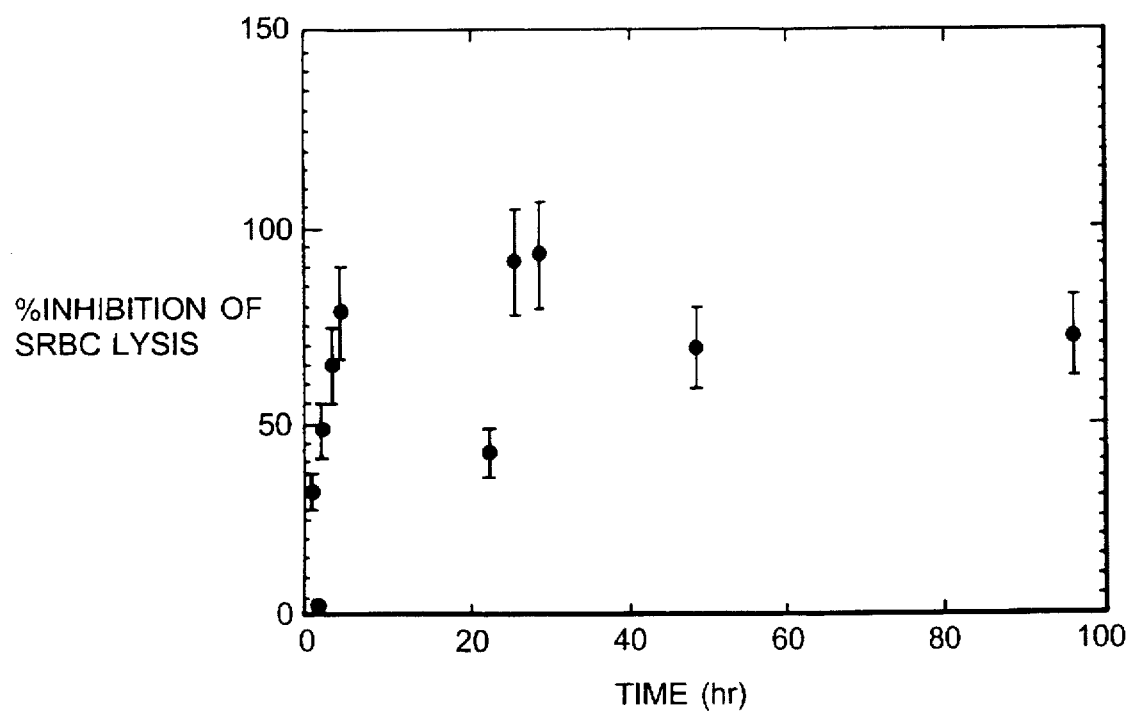
FIG. 3 shows the activity of released sCR1 in medium with time in the practice of the present invention.

Sample aliquots were withdrawn from the incubated mixture at different times and placed in a tube containing 100 µl of 0.1M EDTA solution. Released sCR1 was measured by ELISA as described above. The activity of sCR1 was determined by the inhibition of complement activation as measured by the lysis of sensitized sheep red blood cells (SRBC) (H. F. Weisman, et al., *op. cit.*). The protein was found to maintain its ability throughout the release period. The control samples showed that no sCR1 was released during one week. The in vitro release of sCR1 from the microspheres was thus determined as a function of time. The results of the test are shown in FIGS. 2 and 3.

A model experiment using a biological inactive protein indicated that the protein release was dependent upon the level of collagenase. In a joint cavity where inflammation progresses, the level of collagenase is known to rise (J. Menzel, et al., *Z. Rheumatol.*, 1977, 36, 364–377). Thus, the increased level of collagenase would facilitate in vivo degradation of the microspheres of the present invention in inflammatory lesions.

The invention now being fully described, it will be apparent to one of ordinary skill in the art that many changes and modifications can be made without departing from the spirit or scope of the invention.

We claim:

1. A method of releasing a water soluble pharmaceutically active substance selected from the group consisting of a protein, a peptide, and a glycoprotein, and pharmaceutically acceptable salts and mixtures thereof encapsulated in the form of microspheres by a coating of a crosslinked coacervate of gelatin and chondroitin sulfate wherein the microspheres have a mean diameter of from about 0.5µm to about 100µm and contain from about 10 to about 40 weight percent of the pharmaceutically active substance in vivo in a controlled manner to a host and degrading the coacervates by the action of a collagenase.

2. The method according to claim 1, wherein the crosslinked coacervate is glutaraldehyde-crosslinked.

3. The method according to claim 1, wherein the administration is parenteral.

4. The method according to claim 3, wherein the administration is subcutaneous.

5. The method according to claim 3, wherein the administration is intra-articular.

6. The method according to claim 5, wherein the host is in need of treatment of rheumatoid arthritis.

* * * * *